United States Patent [19]

Mederski et al.

[11] Patent Number: 5,731,321
[45] Date of Patent: Mar. 24, 1998

[54] ENDOTHELIN RECEPTOR ANTAGONISTS

[75] Inventors: Werner Mederski; Mathias Osswald; Dieter Dorsch; Claudia Wilm; Claus J. Schmitges; Maria Christadler, all of Darmstadt, Germany

[73] Assignee: Merck Patent Gesellschaft mit beschrankter Haftung, Darmstadt, Germany

[21] Appl. No.: 691,148

[22] Filed: Aug. 1, 1996

[30] Foreign Application Priority Data

Aug. 2, 1995 [DE] Germany ............ 195 28 418.6

[51] Int. Cl.$^6$ .................. C07D 215/227; C07D 215/20; A61K 31/47
[52] U.S. Cl. .............. 514/291; 514/312; 546/90; 546/153; 546/154; 546/156; 546/157
[58] Field of Search ................... 546/90, 92, 153, 546/156, 157, 154, 168, 169, 170, 171, 172, 176, 183; 514/291, 311, 312, 313, 314

[56] References Cited

U.S. PATENT DOCUMENTS

| | | | |
|---|---|---|---|
| 5,292,740 | 3/1994 | Burri et al. | 514/256 |
| 5,371,226 | 12/1994 | Mederski et al. | 546/156 |
| 5,514,691 | 5/1996 | Chan et al. | 514/312 |
| 5,565,472 | 10/1996 | Hamanaka et al. | 514/312 |

FOREIGN PATENT DOCUMENTS

| | | |
|---|---|---|
| 304 063 | 2/1989 | European Pat. Off. |
| 617 001 | 3/1994 | European Pat. Off. |
| 43 41 663 | 6/1995 | Germany |
| 6340658 | 12/1994 | Japan |
| 93/00879 | 7/1992 | WIPO |
| 94/14434 | 12/1993 | WIPO |
| 95/04534 | 2/1995 | WIPO |

OTHER PUBLICATIONS

Fehnel, Edward A., "Friedländer Syntheses with o-Aminoaryl Ketones . . ", J. Heterocyclic. Chem., vol. 4, No. 4, 1967, pp. 565-570.
Derwent Abstract of JP 6 340 658, 1994.
Matsumori et al., Chemical Abstracts 79:5234v, 1973.

*Primary Examiner*—Mukund J. Shah
*Assistant Examiner*—Deepak R. Rao
*Attorney, Agent, or Firm*—Millen, White, Zelano, & Branigan, P.C.

[57] ABSTRACT

Novel compounds of the formula I

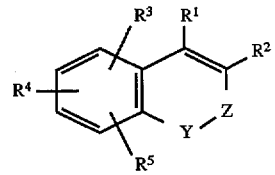

in which

—Y—Z—, $R^1$, $R^2$, $R^3$, $R^4$ and $R^5$ have the meanings as stated in the specification, and their salts show endothelin receptor antagonist properties.

12 Claims, No Drawings

ENDOTHELIN RECEPTOR ANTAGONISTS

The invention relates to compounds of the formula I

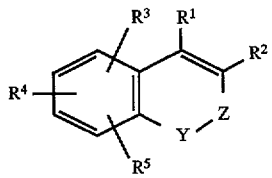

in which

—Y—Z— is —NR$^7$—CO—, —N=C (OR$^7$)— or —N=CR$^8$—,

R$^1$ is Ar,

R$^2$ is COOR$^6$, (CH$_2$)$_n$COOR$^6$, CN, 1H-tetrazol-5-yl or CONHSO$_2$Ar,

R$^3$, R$^4$, R$^5$ are each, independently of one another, R$^6$, OR$^6$, S (O)$_m$R$^6$, Hal, NO$_2$, NR$^6$R$^{6'}$, NHCOR$^6$, NHSO$_2$R$^6$, OCOR$^6$, COR$^6$, COOR$^6$, or CN, where R$^3$ and R$^4$ can together also be an O(CH$_2$)$_n$O group, R$^6$, R$^{6'}$ are each, independently of one another, H, alkyl with 1 to 6 C atoms, benzyl or phenyl, R$^7$ is (CH$_2$)$_n$Ar, R$^8$ is Ar or OAr, Ar are each independently phenyl which is unsubstituted or substituted once, twice or three times by R$^9$, R$^{10}$ or R$^{11}$, or unsubstituted naphthyl or

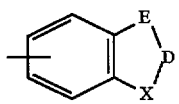

group which is unsubstituted or substituted once or twice in the phenyl moiety by R$^9$ or R$^{10}$, or

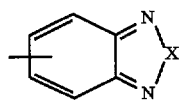

group which is unsubstituted or substituted once or twice in the cyclohexadienyl moiety by R$^9$ or R$^{10}$, R$^9$, R$^{10}$, R$^{11}$ are each, independently of one another, R$^6$, OR$^6$, Hal, CF$_3$, OCF$_3$, OCHF$_2$, OCH$_2$F, NO$_2$, NR$^6$R$^{6'}$, NHCOR$^6$, CN, NHSO$_2$R$^6$, COOR$^6$, COR$^6$, CONHSO$_2$Ar, O(CH$_2$)$_n$R$^2$, O(CH$_2$)$_n$OR$^6$ or S(O)$_m$R$^{6'}$, E is CH$_2$, S or O, D is carbonyl or [C(R$^6$R$^{6'}$)]$_n$, X is O or S, Hal is F, Cl, Br or I, m is 0, 1 or 2, n is 1, 2 or 3, and their salts.

Similar compounds with indane and indene basic frameworks are disclosed in WO 93/08799, those with indole systems are disclosed in WO 94/14434, pyrimidine derivatives are disclosed in EP 0 526 708 A1 and phenyl and naphthyl compounds are disclosed in EP 0 617 001 A1.

The invention was based on the object of finding novel compounds with valuable properties, in particular those which can be used to produce pharmaceuticals.

It has been found that the compounds of the formula I and their salts, while being well tolerated, have very valuable pharmacological properties. In particular, they show endothelin receptor-antagonist properties and can therefore be used for controlling, e.g., treating or preventing, diseases such as hypertension, heart failure, coronary heart disease, renal, cerebral and myocardial ischaemia, renal insufficiency, cerebral infarct, subarachnoid haemorrhage, arteriosclerosis, pulmonary hypertension, inflammations, asthma, prostate hyperplasia, endotoxic shock and for complications after administration of substances such as, for example, cyclosporin, and also other illnesses associated with endothelin activities.

The compounds show, inter alia, a high affinity for the endothelin subreceptors ET$_A$ and ET$_B$. These effects can be determined by customary in vitro or in vivo methods, such as described, for example, by P. D. Stein et al., J. Med. Chem. 37, 1994, 329–331 and E. Ohlstein et al., Proc. Natl. Acad. Sci. USA 91, 1994, 8052–8056.

A suitable method for determining the hypotensive effect is described, for example, by M. K. Bazil et al., J. Cardiovasc. Pharmacol. 22, 1993, 897–905 and J. Lange et al., Lab Animal 20, 1991, Appl. Note 1016.

The compounds of the formula I can be employed as pharmaceutically active compounds in human and veterinary medicine, in particular for the prophylaxis and/or therapy of cardiac, circulatory and vascular disorders, especially hypertension and heart failure.

The invention relates to the compounds of the formula I and their salts, and to a process for the preparation of these compounds and their salts, characterized in that (a) to prepare a compound of the formula I in which —Y—Z— is —NR$^7$—CO— or —N=C (OR$^7$)—, a compound of the formula II

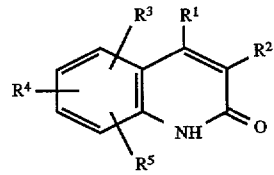

in which

R$^1$, R$^2$, R$^3$, R$^4$ and R$^5$ have the meanings given above, is reacted with a compound of the formula III

R$^7$—Q             III in which

Q is Cl, Br, I or an OH group which is free or reactively functionally modified, and R$^7$ has the meanings stated above, or in that (b) to prepare a compound of the formula I in which —Y—Z— is —N=C (Ar)—, a compound of the formula IV

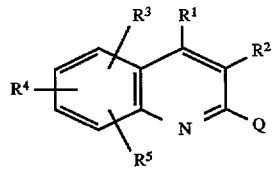

in which

Q is Cl, Br or I, and

R$^1$, R$^2$, R$^3$, R$^4$ and R$^5$ have the meanings given above is reacted with a boron compound of the formula V Ar-BLL'             V in which L, L' are each, independently of one another, OH, $OCH_3$, $OC_2H_5$ or $OC_3H_7$, and Ar has the meanings given above, or in that, c) to prepare a compound of the formula I in which —Y—Z— is —N=C (OAr)—, a compound of the formula IV in which Q is Cl, Br, I or a reactively functionally modified OH group, is reacted with a compound of the formula VI Ar—OH    VI, and/or in that one or more radical(s) $R^1$, $R^2$, $R^3$, $R^4$ and/or $R^5$ in a compound of the formula I are converted into one or more other radical (s) $R^1$, $R^2$, $R^3$, $R^4$ and/or $R^5$ by, for example, i) reducing a nitro group to an amino group, ii) hydrolyzing an ester group to a carboxyl group, iii) converting an amino group by reductive amination into an alkylated amine, iv) converting a carboxyl group into a sulfonamidocarbonyl group, and/or converting a base or acid of the formula I into one of its salts.

The meanings of all radicals which occur several times, such as, for example, $R^6$ and Ar, are independent of one another.

In the above formulae, alkyl has 1 to 6, preferably 1, 2, 3 or 4, C atoms. Alkyl is preferably methyl, also ethyl, propyl, isopropyl, butyl, isobutyl, sec-butyl or tert-butyl, furthermore also pentyl, 1-,2- or 3-methylbutyl, 1,1- or 1,2- or 2,2-dimethylpropyl, 1-ethylpropyl, hexyl, 1-, 2-, 3- or 4-methylpentyl, 1,1-, 1,2-, 1,3-, 2,2- 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

E is, in particular $CH_2$ or O, furthermore also S.

D is, in particular, carbonyl and $CH_2$.

X is preferably O, furthermore preferably S.

m is, in particular, 0, furthermore preferably also 1 and 2.

n is preferably 1, furthermore preferably 2 or 3.

Hal is preferably F, Cl or Br, but also I.

Ar is unsubstituted, preferably-as stated-mono-substituted phenyl, specifically preferably phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-hydroxyphenyl, o-, m- or p-nitrophenyl, o-, m- or p-aminophenyl, o-, m- or p-(N-methylamino)phenyl, o-, m- or p-acetamidophenyl, o-, m- or p-(trifluoromethoxy)phenyl, o-, m- or p-cyanophenyl, o-, m- or p-methoxyphenyl, o-, m- or p-ethoxyphenyl, o-, m- or p-carboxyphenyl, o-, m- or p-methoxycarbonylphenyl, o-, m- or p-ethoxycarbonylphenyl, o-, m- or p-benzyloxycarbonylphenyl, o-, m- or p-(carboxymethyloxy)phenyl, o-, m- or p-(methoxycarbonylmethyloxy)phenyl, o-, m- or p-(methoxycarbonyl-ethyloxy)phenyl, o-, m- or p-(N,N-dimethylamino)phenyl, o-, m- or p-(N-ethylamino)phenyl, o-, m- or p-(N,N-diethylamino)phenyl, o-, m- or p-fluorophenyl, o-, m- or p- bromophenyl, o-, m- or p-chlorophenyl, o-, m- or p-(difluoromethoxy)phenyl, o-m- or p-(fluoromethoxy)phenyl, o-, m- or p-formyl-phenyl, o-, m- or p-acetylphenyl, o-, m- or p-propionyl-phenyl, o-, m- or p-butyrylphenyl, o-, m- or p-pentanoylphenyl, o-, m- or p-(phenylsulfonamidocarbonyl)phenyl, o-, m- or p-phenoxyphenyl, o-, m- or p-methylthiophenyl, o-, m- or p-methylsulfinylphenyl, o-, m- or p-methylsulfonylphenyl, o-, m- or p-benzyloxyphenyl, o-, m- or p-cyanomethyloxyphenyl, furthermore preferably 2,3-methylenedioxyphenyl, 3,4-methylenedioxyphenyl, 2,3-ethylenedioxyphenyl, 3,4-ethylenedioxyphenyl, 6-chloro-3, 4-methylenedioxyphenyl, 2,3-(2-oxo-methylenedioxy) phenyl, 2,3-, 2,4-, 2,5-, 2,6-, 3,4- or 3,5-(difluoromethoxy) -(carboxymethyloxy)-phenyl, 2,3-, 2,4-, 2,5-, 2,6-, 3,4- or 3,5-methoxy(carboxymethyloxy)phenyl, 2,3-, 2,4-, 2,5-, 2,6-, 3,4- or 3,5-hydroxy(carboxymethyloxy)phenyl. Ar is furthermore preferably 2,3-dihydrobenzofuranyl, 2,3-dihydro-2-oxofuranyl-1,3-dithiaindanyl, 2,1,3-benzothiadiazol-4 or 5-yl, 2,1,3-benzoxadiazol-4 or 5-yl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,4- or 2,5-dinitrophenyl, 2,5- or 3,4-dimethoxyphenyl, 3-nitro-4-chlorophenyl, 2-amino-3-chloro-, 2-amino-4-chloro-, 2-amino-5-chloro- or 2-amino-6-chlorophenyl, 2-nitro-4-N, N-dimethylamino- or 3-nitro-4-N,N-dimethylaminophenyl, 3-carboxy-2-methoxy-, 3-carboxy-4-methoxy- or 3-carboxy-5-methoxyphenyl, 2,3,4-, 2,3,5-, 2,3,6-, 2,4,6- or 3,4,5-trichlorophenyl, 2,4,6-tri-tert-butylphenyl, furthermore preferably 2-nitro-4-(trifluoromethyl)phenyl, 3,5-di(trifluoromethyl)phenyl, 2,5-dimethylphenyl, 2-hydroxy-3, 5-dichlorophenyl, 2-fluoro-5- or 4-fluoro-3-(trifluoromethyl)phenyl, 4-chloro-2- or 4-chloro-3-(trifluoromethyl)-, 2-chloro-4- or 2-chloro-5-(trifluoromethyl)phenyl, 4-bromo-2-or 4-bromo-3-(trifluoromethyl)phenyl, p-iodophenyl, 2-nitro-4-methoxyphenyl, 2,5-dimethoxy-4-nitrophenyl, 3,5-dicarboxyphenyl, 2-chloro-3-nitro-5-carboxyphenyl, 4-chloro-3-carboxyphenyl, 2-methyl-5-nitrophenyl, 2,4-dimethyl-3-nitrophenyl, 3,6-dichloro-4-aminophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 3-chloro-4-acetamidophenyl, 4-hydroxy-3-carboxyphenyl, 2-methoxy-5-methylphenyl or 2,4,6-triisopropylphenyl, furthermore naphthyl.

The radical $R^2$ is preferably carbomethoxy, carboethoxy, carbopropoxy, carbobutoxy, carbobenzyloxy, furthermore cyano, 1H-tetrazol-5-yl or phenylsulfonamidocarbonyl, but particularly preferably carboxyl and carboxymethyl.

The radicals $R^3$, $R^4$ and $R^5$ are each, independently of one another, preferably H, methyl, ethyl, propyl, isopropyl, butyl, isobutyl, sec-butyl or tert-butyl, benzyl, F, Cl, Br, methoxy, ethoxy, phenoxy, benzyloxy, nitro or cyano, and are furthermore preferably amino, methylamino, dimethylamino, ethylamino, diethylamino, acetylamino, propionylamino, butyrylamino, methyl-sulfonamido, ethyl sulfonamide, phenylsulfonamido, methylcarbonyloxy, ethylcarbonyloxy, phenylcarbonyloxy, methyloxycarbonyl, ethyloxycarbonyl, methylthio, ethylthio, propylthio, methylsulfinyl, ethylsulfinyl, phenylsulfinyl, methylsulfonyl, ethylsulfonyl or phenylsulfonyl.

The compounds of the formula I may have one or more chiral centers and therefore may occur in different stereoisomeric forms. Formula I embraces all these forms.

Accordingly, the invention relates in particular to those compounds of the formula I in which at least one of the said radicals has one of the meanings indicated above as preferred. Some of the preferred groups of compounds can be expressed by the following part-formulae Ia to Ig which correspond to the formula I and in which the undefined radicals have the meanings stated for formula I, but in which in Ia —Y—Z— is —NR$^7$—CO— or —N=C (OR$^7$)—;

in Ib —Y—Z— is —N=CR$^8$—;

in Ic —Y—Z— is —NR$^7$—CO— and R$^2$ is COOH;

in Id —Y—Z— is —NR$^7$—CO and Ar is a

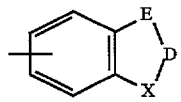

group;

in Ie —Y—Z— is —N=CR$^8$, R$^8$ is Ar and Ar is phenyl which is substituted once, twice or three times by R$^9$, R$^{10}$ or R$^{11}$;

in If —Y—Z— is —NR$^7$—CO— R$^7$ is CH$_2$Ar and Ar is a

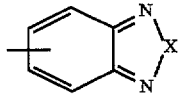

group;

in Ig —Y—Z— is —N=CR$^8$— Ar is a

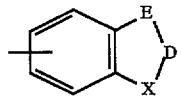

group and

R$^8$ is OAr.

The compounds of the formula I, and the starting materials for preparing them, are moreover prepared by methods known per se, as described in the literature (for example in the standard works such as Houben-Weyl, Methoden der organischen Chemie [Methods of organic chemistry], Georg-Thieme-Verlag, Stuttgart; but especially in WO 94/14434), and specifically under reaction conditions which are known and suitable for the said reactions. It is moreover possible to make use of variants which are known per se but not mentioned in detail here.

The starting materials can, if required, also be formed in situ, so that they are not isolated from the reaction mixture but immediately further converted into the compounds of the formula I.

Compounds of the formula I can preferably be obtained by reacting compounds of the formula II with compounds of the formula III.

In the compounds of the formula III, Q is preferably Cl, Br, I or a reactively modified OH group such as alkylsulfonyloxy with 1–6 C atoms (preferably methylsulfonyloxy) or arylsulfonyloxy with 6–10 C atoms (preferably phenyl-or p-tolylsulfonyloxy).

The reaction takes place, preferably, in an inert solvent in the presence of an acid-binding agent, preferably an alkali metal or alkaline earth metal hydroxide, carbonate or bicarbonate or another salt of a weak acid of the alkali metals or alkaline earth metals, preferably of potassium, sodium, calcium or caesium. The addition of an organic base such as triethylamine, dimethylaniline, pyridine or quinoline or of an excess of the amide component of the formula II or of the alkylating derivative of the formula III may also be beneficial. The reaction time depends on the conditions used and is preferably from a few minutes to 14 days, and the reaction temperature is preferably from about 0° C. to 150° C., normally between 20° and 130°.

Examples of suitable inert solvents are hydrocarbons such as hexane, petroleum ether, benzene, toluene or xylene; chlorinated hydrocarbons such as trichloroethylene, 1,2-dichloroethane, tetrachloro-methane, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methylglycol or ethylglycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate or mixtures of the said solvents.

The starting compounds of the formula II are, as a rule, novel. However, they can be prepared by methods known per se. Thus, for example, methyl 4-(1,3-benzodioxol-5-yl)-1,2-dihydro-2-oxoquinoline-3-carboxylate can be prepared by cyclization of the intermediate produced in the reaction of 1-amino-2-(3,4-methylenedioxybenzoyl)-4-ethoxybenzene and methyl chloroformylacetate in the presence of an inert solvent and of a base. This preferably takes place at temperatures from about 0° C. and about 200° C.; from 30° C. to 80° C. being particularly preferred. Suitable inert solvents and bases are those already mentioned above.

Compounds of the formula I can furthermore be obtained preferably by reacting compounds of the formula IV with compounds of the formula V.

In the compounds of the formula IV, Q is preferably Cl or Br, but also I.

In the compounds of the formula V, L and L' are preferably each, independently of one another, OH, methoxy, ethoxy, propoxy or isopropoxy.

The reaction takes place, preferably, in an inert solvent, in the presence of a base and of a noble metal catalyst. The reaction time depends on the conditions used and is preferably a few minutes to 14 days, and the reaction temperature is preferably from about 0° C. to 150° C., more preferably from 20° C. to 130° C.

Suitable inert solvents and bases are those already mentioned above.

Particularly preferred noble metal catalysts are palladium (0) catalysts such as tetrakis(triphenyl-phosphine)palladium (0).

The starting compounds of the formula IV are, as a rule, novel. However, they can be prepared by methods known per se. Thus, for example, methyl 2-chloro-4-(4-methoxyphenyl) quinoline-3-carboxylate can be prepared from methyl 1,2-dihydro-4-(4-methoxyphenyl)-2-oxoquinoline-3-carboxylate with POCl$_3$. This preferably takes place at temperatures from about 0° C. to about 200° C.; from 30° C. and 80° C. is particularly preferred.

Compounds of the formula I can furthermore preferably be obtained by reacting compounds of the formula IV with compounds of the formula VI.

In the compounds of the formula IV, Q is preferably Cl, Br, I or a reactively modified OH group.

The reaction takes place, preferably, in an inert solvent and with the addition of one of the abovementioned bases.

It is furthermore possible to convert a compound of the formula I into another compound of the formula I by converting one or more radical(s) $R^1$, $R^2$, $R^3$, $R^4$ and/or $R^5$ into one or more other radicals $R^1$, $R^2$, $R^3$, $R^4$ and/or $R^5$, for example by reducing nitro groups, for example by hydrogenation on Raney nickel or Pd/carbon, in an inert solvent such as methanol or ethanol, to amino groups and/or converting an ester group into a carboxy group and/or converting an amino group by reductive amination into an alkylated amine, and/or esterifying carboxyl groups by reaction with alcohols.

It is furthermore possible for free amino groups to be acylated in a conventional way with an acid chloride or anhydride or to be alkylated with an unsubstituted or substituted alkyl halide, preferably in an inert solvent such as dichloromethane or THF and/or in the presence of a base such as triethylamine or pyridine at temperatures preferably from about −60° C. to +30° C.

If required, a functionally modified amino and/or hydroxyl group in a compound of the formula I can be liberated by solvolysis or hydrogenolysis by conventional methods. For example, a compound of the formula I which comprises an $NHCOR^6$ or $COOR^6$ group can be converted into the corresponding compound of the formula I which instead comprises an $NH_2$ or $HOOC$ group. $COOR^6$ groups can be hydrolyzed, for example, with NaOH or KOH in water, water/THF or water/dioxane at temperatures preferably from about 0° C. to 100° C.

A base of the formula I can be converted with an acid into the relevant acid addition salt, for example by reacting equivalent amounts of the base and of the acid in an inert solvent such as ethanol and then evaporating. Particularly suitable acids for this reaction are those which afford physiologically acceptable salts. It is thus possible to use inorganic acids, for example sulfuric acid, nitric acid, hydrohalic acids such as hydrochloric acid or hydrobromic acid, phosphoric acids such as orthophosphoric acid, sulfamic acid, furthermore organic acids, especially aliphatic, alicyclic, araliphatic, aromatic or heterocyclic mono-or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane-or ethanesulfonic acid, ethanedisulfonic acid, 2-hydroxyethanesulfonic acid, benzenesulfonic acid, p-toluenesulfonic acid, naphthalenemono-and disulfonic acids, laurylsulfuric acid. Salts with physiologically unacceptable acids, for example picrates, can be used for isolation and/or purification of the compounds of the formula I.

On the other hand, compounds of the formula I can be converted with bases (for example sodium or potassium hydroxide or carbonate) into the corresponding metal, in particular alkali metal or alkaline earth metal, or into the corresponding ammonium, salts.

The invention furthermore relates to the use of the compounds of the formula I and/or of their physiologically acceptable salts for the production of pharmaceutical compositions, in particular by non-chemical means. For this purpose they may be converted together with at least one solid, liquid and/or semiliquid vehicle or ancillary substance and, if appropriate, in combination with one or more other active substances into a suitable dosage form.

The invention furthermore relates to pharmaceutical compositions comprising at least one compound of the formula I and/or one of its physiologically acceptable salts.

These compositions can be used as pharmaceuticals in human or veterinary medicine. Suitable vehicles are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatin, carbohydrates such as lactose or starch, magnesium stearate, talc, petrolatum. Used for oral administration are, in particular, tablets, pills, coated tablets, capsules, powders, granules, syrups, solutions or drops, for rectal administration are suppositories, for parenteral administration are solutions, preferably oily or aqueous solutions, furthermore suspensions, emulsions or implants, for topical administration are ointments, creams or dusting powders. The novel compounds can also be lyophilized, and the resulting lyophilisates can be used, for example, to produce injection products. The stated compositions can be sterilized and/or comprise ancillary substances such as lubricants, preservatives, stabilizers and/or wetting agents, emulsifiers, salts to influence the osmotic pressure, buffer substances, colorants, flavourings and/or several other active substances, for example one or more vitamins.

Compounds of the formula I and their physiologically acceptable salts can be used to control diseases, in particular hypertension and heart failure.

This entails the substances according to the invention being administered preferably in dosages from about 1 to 500 mg, in particular between 5 to 100 mg per dose unit. The daily dose is preferably from about 0.02 to 10 mg/kg of body weight. However, the specific dose for each patient depends on a wide variety of factors, for example on the activity of the specific compound employed, the age, body weight, general state of health, sex, on the diet, on the time and route of administration, on the rate of excretion, medicinal substance combination and severity of a particular disorder for which the therapy is applied. Oral administration is preferred.

Although the compounds belong to a new class of substances, they may be administered, for example, in a manner and in dosage amounts analogous to ACE inhibitors such a captopril or enalapril.

In the foregoing and in the following examples, all temperatures are set forth uncorrectd in degrees Celsius; and unless otherwise indicated, all parts and percentages are by weight.

All temperatures are stated hereinbefore and hereinafter in °C. In the following examples, "usual working up" means: if necessary, water is added, if necessary, depending on the constitution of the final product, the pH is adjusted to between 2 and 10, extraction is carried out with ethyl acetate or dichloromethane, the organic phase is separated off, dried over sodium sulfate and evaporated, and purification is carried out by chromatography on silica gel, also with separation of the isomers described hereinafter, and/or by crystallization. Rf values on silica gel; mobile phase: ethyl acetate/methanol 9:1.

Mass spectrometry:

EI (electron impact ionization): $M^+$

FAB (Fast Atom Bombardment): $(M+H)^{30}$

EXAMPLE 1

A 50% solution of 0.4 g of 2-methoxybenzyl chloride ("A") in dichloromethane is added to a solution of 0.4 g of methyl 4-(1,3-benzodioxol-5-yl)-1, 2-dihydro-6-ethoxy-2-oxoquinoline-3-carboxylate (obtainable by reacting 1-amino-2-(3,4-methylenedioxybenzoyl)-4-ethoxybenzene and methyl chloroformylacetate in dichloromethane and ethyldiisopropylamine with subsequent cyclization of the intermediate in sodium methanolate solution, m.p. 224°–225°; 1-amino-2-(3,4-methylenedioxybenzoyl)-4-ethoxybenzene is obtainable by reacting 3,4-methylenedioxybenzaldehyde and N-(tert-butyloxycarbonyl)-p-ethoxyaniline, m.p. 113°–114°, in THF, tert-butyllithium at -78°, subsequently oxidizing the resulting 3', 4'-methylenedioxy-2-(N-tert-butyloxy-carbonylamino)-5-ethoxydiphenylmethanol and eliminating the amino protective group, EI-MS 285) in 5 ml of DMF and 0.17 g of potassium carbonate. The reaction mixture is stirred for 4 hours and worked up as usual. This results in the N-alkylation product methyl 4-(1,3-benzodioxol-5-yl)-1,2-dihydro-6-ethoxy-1-(2-methoxybenzyl)-2-oxoquinoline-3-carboxylate, m.p. 182°–183° and the -alkylation product methyl 4-(1,3-benzodioxol-5-yl)-6-ethoxy-2-(2-methoxybenzyloxy) quinoline-3-carboxy-late, m.p. 157°–158°.

Analogously, from the following methyl 4-T-1,2-dihydro-6-ethoxy-2-oxoquinoline-3-carboxylates in which T is 4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl with "A" are obtained the following methyl 4-T-1,2-dihydro-6-ethoxy-1-(2-methoxybenzyl)-2-oxoquinoline-3-carboxylates in which T is 4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethoxy-2-(2-methoxybenzyloxy) quinoline-3-carboxylates in which T is 4-methoxyphenyl
2,4-dimethoxyphenyl
2-benzyloxy-4-methoxyphenyl
2-hydroxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 3-methoxybenzyl chloride with the following methyl 4-T-1,2-dihydro-6-ethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethoxy-1-(3-methoxybenzyl)-2-oxoquinoline-3-carboxylates in which T is 1,3-benzodioxol-5-yl, m.p. 138°–139°
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethoxy-2-(3-methoxybenzyloxy) quinoline-3-carboxylates in which T is 1,3-benzodioxol-5-yl, m.p. 139°–140°
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 4-methoxybenzyl chloride with the following methyl 4-T-1,2-dihydro-6-ethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethoxy-1-(4-methoxybenzyl)-2-oxoquinoline-3-carboxylates in which T is 1,3-benzodioxol-5-yl, m.p. 157°–158°
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethoxy-2-(4-methoxybenzyloxy) quinoline-3-carboxylates in which T is 1,3-benzodioxol-5-yl, m.p. 141°–142°
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 3,4-methylenedioxybenzyl chloride with the following methyl 4-T-1,2-dihydro-6-ethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethoxy-1-(3,4-methylenedioxybenzyl)-2-oxoquinoline-3-carboxylates in which T is 1,3-benzodioxol-5-yl, m.p. 177°–178°
4-methoxyphenyl
2,4-dimethoxyphenyl
2-benzyloxy-4-methoxyphenyl
2-hydroxy-4-methoxyphenyl
2-carboxymethoxy-4-methoxyphenyl 2-hydroxyethyloxy-4-methoxyphenyl
and the following methyl 4-T-6-ethoxy-2-(3,4-methylenedioxybenzyloxy)quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 6-chloro-3,4-methylenedioxybenzyl chloride with the following methyl 4-T-1,2-dihydro-6-ethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethoxy-1-(6-chloro-3,4-methylenedioxybenzyl)-2-oxoquin-oline-3-carboxylates in which T is 1,3-benzodioxol-5-yl, m.p. 207°–208°
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethoxy-2-(6-chloro-3,4-methylenedioxybenzyloxy)quinoline-3-carboxylates in which T is 1,3-benzodioxol-5-yl, m.p. 200°–201°
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of benzyl chloride with the following methyl 4-T-1,2-dihydro-6-ethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1, 2-dihydro-6-ethoxy-1-benzyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethoxy-2-benzyloxyquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2-(methylthio)benzyl chloride with the following methyl 4-T-1,2-dihydro-6-ethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethoxy-1-(2-methylthiobenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethoxy-2-(2-methylthiobenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2-(methylsulfinyl)benzyl chloride with the following methyl 4-T-1,2-dihydro-6-ethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethoxy-1-(2-methylsulfinylbenzyl)-2-oxoquinoline -3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl 2-carboxymethoxy-4-methoxyphenyl
2-hydroxyethyloxy-4-methoxyphenyl and the following methyl 4-T-6-ethoxy-2-(2-methylsulfinylbenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2-(methylsulfonyl)benzyl chloride with the following methyl 4-T-1,2-dihydro-6-ethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethoxy-1-(2-methylsulfonylbenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethoxy-2-(2-methylsulfonylbenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2,3-dimethoxybenzyl chloride with the following methyl 4-T-1,2-dihydro-6-ethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethoxy-1-(2,3-dimethoxybenzyl)-2-oxoquinoline-3-carboxylates in which T is 1,3-benzodioxol-5-yl, m.p. 180°–181°
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethoxy-2-(2,3-dimethoxybenzyloxy) quinoline-3-carboxylates in which T is 1,3-benzodioxol-5-yl, m.p. 133°–134°
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2,3-methylenedioxybenzyl chloride with the following methyl 4-T-1,2-dihydro-6-ethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethoxy-1-(2,3-methylenedioxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethoxy-2-(2,3-methylenedioxybenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2,1,3-benzothiadiazole-5-methyl chloride with the following methyl 4-T-1,2-dihydro-6-ethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethoxy-1-(2,1,3-benzothiadiazole-5-methyl)-2-oxoquinoline-3-carboxylates in which T is 1,3-benzodioxol-5-yl
4-methoxyphenyl
2,4-dimethoxyphenyl 2-benzyloxy-4-methoxyphenyl
2-hydroxy-4-methoxyphenyl
2-carboxymethoxy-4-methoxyphenyl
2-hydroxyethyloxy-4-methoxyphenyl
and the following methyl 4-T-6-ethoxy-2-(2,1,3-benzothiadiazole-5-methyloxy)quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, from the following methyl 4-T-1,2-dihydro-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl with "A" are obtained the following methyl 4-T-1,2-dihydro-1-(2-methoxybenzyl)-2-oxoquinoline-3-carboxylates in which T is 1,3-benzodioxol-5-yl, m.p. 178°–179°
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-2-(2-methoxy-benzyloxy)quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl.
2-hydroxyethyloxy-4-methoxyphenyl.

Analogously, reaction of 3-methoxybenzyl chloride with the following methyl 4-T-1,2-dihydro-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-1-(3-methoxybenzyl)-2-oxoquinoline-3-carboxylates in which T is 1,3-benzodioxol-5-yl, m.p. 162°–163°
4-methoxyphenyl
2,4-dimethoxyphenyl
2-benzyloxy-4-methoxyphenyl 2-hydroxy-4-methoxyphenyl
2-carboxymethoxy-4-methoxyphenyl
2-hydroxyethyloxy-4-methoxyphenyl
and the following methyl 4-T-2-(3-methoxy-benzyloxy)quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 4-methoxybenzyl chloride with the following methyl 4-T-1,2-dihydro-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-1-(4-methoxybenzyl)-2-oxoquinoline-3-carboxylates in which T is 1,3-benzodioxol-5-yl, m.p. 214°–215°
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-2-(4-methoxy-benzyloxy)quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 3,4-methylenedioxybenzyl chloride with the following methyl 4-T-1,2-dihydro-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-1-(3,4-methylenedioxybenzyl)-2-oxoquinoline-3-carboxylates in which T is 1,3-benzodioxol-5-yl, m.p. 192°–193°
4-methoxyphenyl
2,4-dimethoxyphenyl
2-benzyloxy-4-methoxyphenyl
2-hydroxy-4-methoxyphenyl 2-carboxymethoxy-4-methoxyphenyl
2-hydroxyethyloxy-4-methoxyphenyl and the following methyl 4-T-2-(3,4-methylenedioxybenzyloxy)quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 6-chloro-3,4-methylenedioxybenzyl chloride with the following methyl 4-T-1,2-dihydro-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-1-(6-chloro-3,4-methylenedioxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-2-(6-chloro-3,4-methylenedioxybenzyloxy)quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of benzyl chloride with the following methyl 4-T-1,2-dihydro-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-1-benzyl-2-oxoquinoline-3-carboxylates in which T is 1,3-benzodioxol-5-yl, m.p. 139°–140°
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-2-benzyloxyquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2-methylthiobenzyl chloride with the following methyl 4-T-1,2-dihydro-2-oxo-quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-1-(2-methylthiobenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-2-(2-methylthiobenzyloxy)quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2-methylsulfinylbenzyl chloride with the following methyl 4-T-1,2-dihydro-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-1-(2-methylsulfinylbenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl 2-carboxymethoxy-4-methoxyphenyl
2-hydroxyethyloxy-4-methoxyphenyl
and the following methyl 4-T-2-(2-methylsulfinylbenzyloxy) quinoline-3-carboxylates in which T is
1,3-benzodioxol-5-yl
4-methoxyphenyl
2,4-dimethoxyphenyl.
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2-methylsulfonylbenzyl chloride with the following methyl 4-T-1,2-dihydro-2-oxoquinoline-3-carboxylates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
results in the following methyl 4-T-1,2-dihydro-1-(2-methylsulfonylbenzyl)-2-oxoquinoline-3-carboxylates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
and the following methyl 4-T-2-(2-methylsulfonylbenzyloxy) quinoline-3-carboxylates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2,3-dimethoxybenzyl chloride with the following methyl 4-T-1,2-dihydro-2-oxoquinoline-3-carboxylates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
results in the following methyl 4-T-1,2-dihydro-1-(2,3-dimethoxybenzyl)-2-oxoquinoline-3-carboxylates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
and the following methyl 4-T-2-(2,3-dimethoxybenzyloxy) quinoline-3-carboxylates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2,3-methylenedioxybenzyl chloride with the following methyl 4-T-1,2-dihydro-2-oxoquinoline-3-carboxylates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
results in the following methyl 4-T-1,2-dihydro-1-(2,3-methylenedioxybenzyl)-2-oxoquinoline-3-carboxylates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
and the following methyl 4-T-2-(2,3-methylenedioxybenzyloxy) quinoline-3-carboxylates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, from the following methyl 4-T-1,2-dihydro-6-propionyl-2-oxoquinoline-3-carboxylates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
with "A" are obtained the following methyl 4-T-1,2-dihydro-1-(2-methoxybenzyl)-6-propionyl-2-oxoquinoline-3-carboxylates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl 2-hydroxyethyloxy-4-methoxyphenyl
and the following methyl 4-T-2-(2-methoxybenzyloxy)-6-propionylquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl.

Analogously, reaction of 3-methoxybenzyl chloride with the following methyl 4-T-1,2-dihydro-6-propionyl-2-oxoquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
results in the following methyl 4-T-1,2-dihydro-1-(3-methoxybenzyl)-6-propionyl-2-oxoquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
and the following methyl 4-T-2-(3-methoxybenzyloxy)-6-propionylquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl.

Analogously, reaction of 4-methoxybenzyl chloride with the following methyl 4-T-1,2-dihydro-6-propionyl-2-oxoquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
results in the following methyl 4-T-1,2-dihydro-1-(4-methoxybenzyl)-6-propionyl-2-oxoquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
and the following methyl 4-T-2-(4-methoxybenzyloxy)-6-propionylquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl.

Analogously, reaction of 3,4-methylenedioxybenzyl chloride with the following methyl 4-T-1,2-dihydro-6-propionyl-2-oxoquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
results in the following methyl 4-T-1,2-dihydro-1-(3,4-methylenedioxybenzyl)-6-propionyl-2-oxoquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
and the following methyl 4-T-2-(3,4-methylenedioxybenzyloxy)-6-propionylquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl.

Analogously, reaction of 6-chloro-3,4-methylenedioxybenzyl chloride with the following methyl 4-T-1,2-dihydro-6-propionyl-2-oxoquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
results in the following methyl 4-T-1,2-dihydro-1-(6-chloro-3,4-methylenedioxybenzyl)-6-propionyl-2-oxoquinoline-3-carboxylates in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl 2-hydroxyethyloxy-4-methoxyphenyl and the following methyl 4-T-2-(6-chloro-3,4-methylenedioxybenzyloxy)-6-propionylquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of benzyl chloride with the following methyl 4-T-1,2-dihydro-6-propionyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-1-benzyl-6-propionyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-2-benzyloxy-6-propionyl-quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, from the following methyl 4-T-1,2-dihydro-6,7-dimethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl with "A" are obtained the following methyl 4-T-1,2-dihydro-6,7-dimethoxy-1-(2-methoxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6,7-dimethoxy-2-(2-methoxybenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 3-methoxybenzyl chloride with the following methyl 4-T-1,2-dihydro-6,7-dimethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6,7-dimethoxy-1-(3-methoxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6,7-dimethoxy-2-(3-methoxybenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 4-methoxybenzyl chloride with the following methyl 4-T-1,2-dihydro-6,7-dimethoxy-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6,7-dimethoxy-1-(4-methoxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6,7-dimethoxy-2-(4-methoxybenzyloxy) quinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl.

Analogously, reaction of 3,4-methylenedioxybenzyl chloride with the following methyl 4-T-1,2-dihydro-6,7-dimethoxy-2-oxoquinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl results in the following methyl 4-T-1,2-dihydro-6,7-dimethoxy-1-(3,4-methylenedioxybenzyl)-2-oxoquinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl and the following methyl 4-T-6,7-dimethoxy-2-(3,4-methylenedioxybenzyloxy)quinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl.

Analogously, reaction of 6-chloro-3,4-methylenedioxybenzyl chloride with the following methyl 4-T-1,2-dihydro-6,7-dimethoxy-2-oxoquinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl results in the following methyl 4-T-1,2-dihydro-6,7-dimethoxy-1-(6-chloro-3,4-methylenedioxybenzyl)-2-oxoquinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl and the following methyl 4-T-6,7-dimethoxy-2-(6-chloro-3,4-methylenedioxybenzyloxy) quinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl.

Analogously, reaction of benzyl chloride with the following methyl 4-T-1,2-dihydro-6,7-dimethoxy-2-oxoquinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl results in the following methyl 4-T-1,2-dihydro-6,7-dimethoxy-1-benzyl-2-oxo-quinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl and the following methyl 4-T-2-benzyloxy-6,7-dimethoxyquinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl.

Analogously, from the following methyl 4-T-1,2-dihydro-6,7-dimethyl-2-oxoquinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl with "A" are obtained the following methyl 4-T-1,2-dihydro-6,7-dimethyl-1-(2-methoxybenzyl)-2-oxoquinoline-3-carboxylates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl and the following methyl 4-T-6,7-dimethyl-2-(2-methoxybenzyloxy) quinoline-3-carboxylates in which T is 1,3-benzodioxol-5-yl 4-methoxyphenyl 2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 3-methoxybenzyl chloride with the following methyl 4-T-1,2-dihydro-6,7-dimethyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6,7-dimethyl-1-(3-methoxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6,7-dimethyl-2-(3-methoxybenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 4-methoxybenzyl chloride with the following methyl 4-T-1,2-dihydro-6,7-dimethyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6,7-dimethyl-1-(4-methoxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6,7-dimethyl-2-(4-methoxybenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 3,4-methylenedioxybenzyl chloride with the following methyl 4-T-1,2-dihydro-6,7-dimethyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6,7-dimethyl-1-(3,4-methylenedioxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6,7-dimethyl-2-(3,4-methylenedioxybenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 6-chloro-3,4-methylenedioxybenzyl chloride with the following methyl 4-T-1,2-dihydro-6,7-dimethyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6,7-dimethyl-1-(6-chloro-3,4-methylenedioxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6,7-dimethyl-2-(6-chloro-3,4-methylenedioxybenzyloxy) quinoline-3-carboxylates in which T is 1,3-benzodioxol-5-yl
4-methoxyphenyl 2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of benzyl chloride with the following methyl 4-T-1,2-dihydro-6,7-dimethyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6,7-dimethyl-1-benzyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-2-benzyloxy-6,7-dimethyl-quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, from the following methyl 4-T-1,2-dihydro-6,-ethyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl with "A" are obtained the following methyl 4-T-1,2-dihydro-6-ethyl-1-(2-methoxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethyl-2-(2-methoxybenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl Analogously, reaction of 3-methoxybenzyl chloride with the following methyl 4-T-1,2-dihydro-6-ethyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethyl-1-(3-methoxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethyl-2-(3-methoxybenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 4-methoxybenzyl chloride with the following methyl 4-T-1,2-dihydro-6-ethyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethyl-1-(4-methoxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethyl-2-(4-methoxybenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl 2-carboxymethoxy-4-methoxyphenyl
2-hydroxyethyloxy-4-methoxyphenyl.

Analogously, reaction of 3,4-methylenedioxybenzyl chloride with the following methyl 4-T-1,2-dihydro-6-ethyl-2-oxoquinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl results in the following methyl 4-T-1,2-dihydro-6-ethyl-1-(3,4-methylenedioxybenzyl)-2-oxoquinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl and the following methyl 4-T-6-ethyl-2-(3,4-methylenedioxybenzyloxy)quinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl.

Analogously, reaction of 6-chloro-3,4-methylenedioxybenzyl chloride with the following methyl 4-T-1,2-dihydro-6-ethyl-2-oxoquinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl results in the following methyl 4-T-1,2-dihydro-6-ethyl-1-(6-chloro-3,4-methylenedioxybenzyl)-2-oxoquinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl and the following methyl 4-T-6-ethyl-2-(6-chloro-3,4-methylenedioxybenzyloxy) quinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl.

Analogously, reaction of benzyl chloride with the following methyl 4-T-1,2-dihydro-6-ethyl-2-oxoquinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl results in the following methyl 4-T-1,2-dihydro-6-ethyl-1-benzyl-2-oxoquinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl and the following methyl 4-T-6-ethyl-2-benzyloxyquinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl.

Analogously, reaction of 2-methylthiobenzyl chloride with the following methyl 4-T-1,2-dihydro-6-ethyl-2-oxoquinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl results in the following methyl 4-T-1,2-dihydro-6-ethyl-1-(2-methylthiobenzyl)-2-oxoquinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl and the following methyl 4-T-6-ethyl-2-(2-methylthiobenzyloxy) quinoline-3-carboxylates in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl 2-carboxymethoxy-4-methoxyphenyl
2-hydroxyethyloxy-4-methoxyphenyl.

Analogously, reaction of 2-methylsulfinylbenzyl chloride with the following methyl 4-T-1,2-dihydro-6-ethyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethyl-1-(2-methylsulfinylbenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethyl-2-(2-methylsulfinylbenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2-methylsulfonylbenzyl chloride with the following methyl 4-T-1,2-dihydro-6-ethyl-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethyl-1-(2-methylsulfonylbenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethyl-2-(2-methylsulfonylbenzyloxy) quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2,3-dimethoxybenzyl chloride with the following methyl 4-T-6-ethyl-1,2-dihydro-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethyl-1-(2,3-dimethoxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethyl-2-(2,3-dimethoxybenzyloxy)quinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 2,3-methylenedioxybenzyl chloride with the following methyl 4-T-6-ethyl-1,2-dihydro-2-oxoquinoline-3-carboxylates in which T is 1,3-benzodioxol-5-yl
4
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl results in the following methyl 4-T-1,2-dihydro-6-ethyl-1-(2,3-methylenedioxybenzyl)-2-oxoquinoline-3-carboxylates in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the following methyl 4-T-6-ethyl-2-(2,3-methylenedioxybenzyloxy) quinoline-3-carboxylates in which T is 1,3-benzodioxol-5-yl
4-methoxyphenyl 4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

EXAMPLE 2

A solution of 0.5 g of methyl 4-(1,3-benzodioxol-5-yl)-1,2-dihydro-6-ethoxy-1-(2-methoxybenzyl)-2-oxoquinoline-3-carboxylate and 6 ml of 5N KOH in 10 ml of methanol is boiled under reflux for 2 hours. The usual working up results in 4-(1,3-benzodioxol-5-yl)-1,2-dihydro-6-ethoxy-1-(2-methoxybenzyl)-2-oxoquinoline-3-carboxylic acid, m.p. 225°–226°. Analogously, the O-alkylation product 4-(1,3-benzodioxol-5-yl)-6-ethoxy-2-(2-methoxybenzyloxy)quinoline-3-carboxylic acid is obtained from methyl 4-(1,3-benzodioxol-5-yl)-6-ethoxy-2-(2-methoxybenzyloxy) quinoline-3-carboxylate.

Analogously, from the following methyl 4-T-1,2-dihydro-6-ethoxy-1-(2-methoxybenzyl)-2-oxoquinoline-3-carboxylates and methyl 4-T-6-ethoxy-2-(2-methoxybenzyloxy) quinoline-3-carboxylates, in which T is 4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl and the methyl 4-T-1,2-dihydro-6-ethoxy-1-(3-methoxybenzyl)-2-oxoquinoline-3-carboxylates,
methyl 4-T-6-ethoxy-2-(3-methoxybenzyloxy) quinoline-3-carboxylates,
methyl 4-T-1,2-dihydro-6-ethoxy-1-(4-methoxybenzyl)-2-oxoquinoline-3-carboxylates,
methyl 4-T-6-ethoxy-2-(4-methoxybenzyloxy)quinoline-3-carboxylates,
methyl 4-T-1,2-dihydro-6-ethoxy-1-(3,4-methylenedioxybenzyl)-2-oxoquinoline-3-carboxylates,
methyl 4-T-6-ethoxy-2-(3,4-methylenedioxybenzyloxy)-quinoline-3-carboxylates,
methyl 4-T-1,2-dihydro-6-ethoxy-1-(6-chloro-3,4-methylenedioxybenzyl)-2-oxoquinoline-3-carboxylates,
methyl 4-T-6-ethoxy-2-(6-chloro-3,4-methylenedioxybenzyloxy)quinoline-3-carboxylates,
methyl 4-T-1,2-dihydro-6-ethoxy-1-benzyl-2-oxoquinoline-3-carboxylates,
methyl 4-T-6-ethoxy-2-benzyloxyquinoline-3-carboxylates,
methyl 4-T-1,2-dihydro-6-ethoxy-1-(2-methylthiobenzyl-2-oxoquinoline-3-carboxylates,
methyl 4-T-6-ethoxy-2-(2-methylthiobenzyloxy) quinoline-3-carboxylates,
methyl 4-T-1,2-dihydro-6-ethoxy-1-(2-methylsulfinylbenzyl)-2-oxoquinoline-3-carboxylates,
methyl 4-T-6-ethoxy-2-(2-methylsulfinylbenzyloxy) quinoline-3-carboxylates,
methyl 4-T-1,2-dihydro-6-ethoxy-1-(2-methylsulfonylbenzyl)-2-oxoquinoline-3-carboxylates,
methyl 4-T-6-ethoxy-2-(2-methylsulfonylbenzyloxy) quinoline-3-carboxylates,
methyl 4-T-1,2-dihydro-6-ethoxy-1-(2,3-dimethoxybenzyl)-2-oxoquinoline-3-carboxylates,
methyl 4-T-6-ethoxy-2-(2,3-dimethoxybenzyloxy) quinoline-3-carboxylates,
methyl 4-T-1,2-dihydro-6-ethoxy-1-(2,3-methylenedioxybenzyl)-2-oxoquinoline-3-carboxylates,
methyl 4-T-6-ethoxy-2-(2,3-methylenedioxybenzyloxy)-quinoline-3-carboxylates,
methyl 4-T-1,2-dihydro-6-ethoxy-1-(2,1,3-benzothiadiazol-5-methyl)-2-oxo-quinoline-3-carboxylates,
methyl 4-T-6-ethoxy-2-(2,1,3-benzothiadiazol-5-methyloxy)quinoline-3-carboxylates,
methyl 4-T-1,2-dihydro-1-(2-methoxybenzyl)-2-oxoquinoline-3-carboxylates,
methyl 4-T-2-(2-methoxybenzyloxy)quinoline-3-carboxylates,
methyl 4-T-1,2-dihydro-1-(3-methoxybenzyl)-2-oxoquinoline-3-carboxylates,
methyl 4-T-2-(3-methoxybenzyloxy)quinoline-3-carboxylates,
methyl 4-T-1,2-dihydro-1-(4-methoxybenzyl)-2-oxoquinoline-3-carboxylates,
methyl 4-T-2-(4-methoxybenzyloxy)quinoline-3-carboxylates,
methyl 4-T-1,2-dihydro-1-(3,4-methylenedioxybenzyl)-2-oxoquinoline-3-carboxylates,
methyl 4-T-2-(3,4-methylenedioxybenzyloxy)quinoline-3-carboxylates,
methyl 4-T-1,2-dihydro-1-(6-chloro-3,4-methylenedioxybenzyl)-2-oxoquinoline-3-carboxylates,
methyl 4-T-2-(6-chloro-3,4-methylenedioxybenzyloxy)-quinoline-3-carboxylates,
methyl 4-T-1,2-dihydro-1-benzyl-2-oxoquinoline-3-carboxylates,
methyl 4-T-2-benzyloxyquinoline-3-carboxylates,
methyl 4-T-1,2-dihydro-1-(2-methylthiobenzyl)-2-oxoquinoline-3-carboxylates,
methyl 4-T-2-(2-methylthiobenzyloxy)quinoline-3-carboxylates,
methyl 4-T-1,2-dihydro-1-(2-methylsulfinylbenzyl)-2-oxoquinoline-3-carboxylates,
methyl 4-T-2-(2-methylsulfinylbenzyloxy)quinoline-3-carboxylates,
methyl 4-T-1,2-dihydro-1-(2-methylsulfonylbenzyl)-2-oxoquinoline-3-carboxylates,
methyl 4-T-2-(2-methylsulfonylbenzyloxy)quinoline-3-carboxylates,
methyl 4-T-1,2-dihydro-1-(2,3-dimethoxybenzyl)-2-oxo-quinoline-3-carboxylates,
methyl 4-T-2-(2,3-dimethoxybenzyloxy)quinoline-3-carboxylates,
methyl 4-T-1,2-dihydro-1-(2,3-methylenedioxybenzyl)-2-oxoquinoline-3-carboxylates,
methyl 4-T-2-(2,3-methylenedioxybenzyloxy)quinoline-3-carboxylates,
methyl 4-T-1,2-dihydro-1-(2,1,3-benzothiadiazole-5-methyl)-2-oxoquinoline-3-carboxylates,
methyl 4-T-2-(2,1,3-benzothiadiazole-5-methyloxy) quinoline-3-carboxylates,
methyl 4-T-1,2-dihydro-1-(2-methoxybenzyl)-6-propionyl-2-oxoquinoline-3-carboxylates,
methyl 4-T-2-(2-methoxybenzyloxy)-6-propionylquinoline-3-carboxylates,
methyl 4-T-1,2-dihydro-1-(3-methoxybenzyl)-6-propionyl-2-oxoquinoline-3-carboxylates,
methyl 4-T-2-(3-methoxybenzyloxy)-6-propionylquinoline-3-carboxylates,
methyl 4-T-1,2-dihydro-1-(4-methoxybenzyl)-6-propionyl-2-oxoquinoline-3-carboxylates,
methyl 4-T-2-(4-methoxybenzyloxy)-6-propionylquinoline-3-carboxylates,
methyl 4-T-1,2-dihydro-1-(3,4-methylenedioxybenzyl)-6-propionyl-2-oxoquinoline-3-carboxylates, methyl 4-T-2-(3,4-methylenedioxybenzyloxy)-6-propionyl-quinoline-3-carboxylates, methyl 4-T-1,2-dihydro-1-(6-chloro-3,4-methylenedioxybenzyl)-6-propionyl-2-oxoquinoline-3-carboxylates, methyl 4-T-2-(6-chloro-3,4-methylenedioxybenzyloxy)-6-propionylquinoline-3-carboxylates, methyl 4-T-1,2-dihydro-1-benzyl-6-propionyl-2-oxoquinoline-3-carboxylates, methyl 4-T-2-benzyloxy-6-propionylquinoline-3-carboxylates, methyl 4-T-1,2-dihydro-6,7-dimethoxy-1-(2-methoxybenzyl)-2-oxoquinoline-3-carboxylates, methyl 4-T-6,7-dimethoxy-2-(2-methoxybenzyloxy)quinoline-3-carboxylates, methyl 4-T-1,2-dihydro-6,7-dimethoxy-1-(3-methoxybenzyl)-2-oxoquinoline-3-carboxylates, methyl 4-T-6,7-dimethoxy-2-(3-methoxybenzyloxy)quinoline-3-carboxylates, methyl 4-T-1,2-dihydro-6,7-dimethoxy-1-(4-methoxybenzyl)-2-oxoquinoline-3-carboxylates, methyl 4-T-6,7-dimethoxy-2-(4-methoxybenzyloxy)quinoline-3-carboxylates, methyl 4-T-1,2-dihydro-6,7-dimethoxy-1-(3,4-methylenedioxybenzyl)-2-oxoquinoline-3-carboxylates, methyl 4-T-6,7-dimethoxy-2-(3,4-methylenedioxybenzyloxy)quinoline-3-carboxylates, methyl 4-T-1,2-dihydro-6,7-dimethoxy-1-(6-chloro-3,4-methylenedioxybenzyl)-2-oxoquinoline-3-carboxylates, methyl 4-T-6,7-dimethoxy-2-(6-chloro-3,4-methylenedioxybenzyloxy)quinoline-3-carboxylates, methyl 4-T-1,2-dihydro-6,7-dimethoxy-1-benzyl-2-oxoquinoline-3-carboxylates, methyl 4-T-2-benzyloxy-6,7-dimethoxyquinoline-3-carboxylates, methyl 4-T-1,2-dihydro-6,7-dimethyl-1-(2-methoxybenzyl)-2-oxoquinoline-3-carboxylates, methyl 4-T-6,7-dimethyl-2-(2-methoxybenzyloxy)quinoline-3-carboxylates, methyl 4-T-1,2-dihydro-6,7-dimethyl-1-(3-methoxybenzyl)-2-oxoquinoline-3-carboxylates, methyl 4-T-6,7-dimethyl-2-(3-methoxybenzyloxy)quinoline-3-carboxylates, methyl 4-T-1,2-dihydro-6,7-dimethyl-1-(4-methoxybenzyl)-2-oxoquinoline-3-carboxylates, methyl 4-T-6,7-dimethyl-2-(4-methoxybenzyloxy)quinoline-3-carboxylates, methyl 4-T-1,2-dihydro-6,7-dimethyl-1-(3,4-methylenedioxybenzyl)-2-oxoquinoline-3-carboxylates, methyl 4-T-6,7-dimethyl-2-(3,4-methylenedioxybenzyloxy)quinoline-3-carboxylates, methyl 4-T-1,2-dihydro-6,7-dimethyl-1-(6-chloro-3,4-methylenedioxybenzyl)-2-oxoquinoline-3-carboxylates, methyl 4-T-6,7-dimethyl-2-(6-chloro-3,4-methylenedioxybenzyloxy)quinoline-3-carboxylates, methyl 4-T-1,2-dihydro-6,7-dimethyl-1-benzyl-2-oxoquinoline-3-carboxylates, methyl 4-T-2-benzyloxy-6,7-dimethylquinoline-3-carboxylates, methyl 4-T-1,2-dihydro-6-ethyl-1-(2-methoxybenzyl)-2-oxoquinoline-3-carboxylates, methyl 4-T-6-ethyl-2-(2-methoxybenzyloxy)quinoline-3-carboxylates, methyl 4-T-1,2-dihydro-6-ethyl-1-(3-methoxybenzyl)-2-oxoquinoline-3-carboxylates, methyl 4-T-6-ethyl-2-(3-methoxybenzyloxy)quinoline-3-carboxylates, methyl 4-T-1,2-dihydro-6-ethyl-1-(4-methoxybenzyl)-2-oxoquinoline-3-carboxylates, methyl 4-T-6-ethyl-2-(4-methoxybenzyloxy)quinoline-3-carboxylates, methyl 4-T-1,2-dihydro-6-ethyl-1-(3,4-methylenedioxybenzyl)-2-oxoquinoline-3-carboxylates, methyl 4-T-6-ethyl-2-(3,4-methylenedioxybenzyloxy)-quinoline-3-carboxylates, methyl 4-T-1,2-dihydro-6-ethyl-1-(6-chloro-3,4-methylenedioxybenzyl)-2-oxoquinoline-3-carboxylates, methyl 4-T-6-ethyl-2-(6-chloro-3,4-methylenedioxybenzyloxy)quinoline-3-carboxylates, methyl 4-T-1,2-dihydro-6-ethyl-1-benzyl-2-oxoquinoline-3-carboxylates, methyl 4-T-6-ethyl-2-benzyloxyquinoline-3-carboxylates, methyl 4-T-1,2-dihydro-6-ethyl-1-(2-methylthiobenzyl)-2-oxoquinoline-3-carboxylates, methyl 4-T-6-ethyl-2-(2-methylthiobenzyloxy)quinoline-3-carboxylates, methyl 4-T-1,2-dihydro-6-ethyl-1-(2-methylsulfinylbenzyl)-2-oxoquinoline-3-carboxylates, methyl 4-T-6-ethyl-2-(2-methylsulfinylbenzyloxy)quinoline-3-carboxylates, methyl 4-T-1,2-dihydro-6-ethyl-1-(2-methylsulfonylbenzyl)-2-oxoquinoline-3-carboxylates, methyl 4-T-6-ethyl-2-(2-methylsulfonylbenzyloxy)quinoline-3-carboxylates, methyl 4-T-1,2-dihydro-6-ethyl-1-(2,3-dimethoxybenzyl)-2-oxoquinoline-3-carboxylates, methyl 4-T-6-ethyl-2-(2,3-dimethoxybenzyloxy)quinoline-3-carboxylates, methyl 4-T-1,2-dihydro-6-ethyl-1-(2,3-methylenedioxybenzyl)-2-oxo-quinoline-3-carboxylates, methyl 4-T-6-ethyl-2-(2,3-methylenedioxybenzyloxy)quinoline-3-carboxylates, methyl 4-T-1,2-dihydro-6-ethyl-1-(2,1,3-benzothiadiazole-5-methyl)-2-oxoquinoline-3-carboxylates and methyl 4-T-6-ethyl-2-(2,1,3-benzothiadiazole-5-methyloxy)quinoline-3-carboxylates, in which T is 1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl are obtained the following 4-T-1,2-dihydro-6-ethoxy-1-(2-methoxybenzyl)-2-oxoquinoline-3-carboxylic acids in which T is 4-methoxyphenyl, m.p. 234.5°
2,4-dimethoxyphenyl, m.p. 220°–221°
2-benzyloxy-4-methoxyphenyl
2-hydroxy-4-methoxyphenyl
2-carboxymethoxy-4-methoxyphenyl
2-hydroxyethyloxy-4-methoxyphenyl 4-T-6-ethoxy-2-(2-methoxybenzyloxy)quinoline-3-carboxylic acids in which T is 4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl 4-T-1,2-dihydro-6-ethoxy-1-(3-methoxybenzyl)-2-oxoquinoline-3-carboxylic acids in which T is
  1,3-benzodioxol-5-yl, m.p. 174°–175°
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-6-ethoxy-2-(3-methoxybenzyloxy)quinoline-3-carboxylic acids in which T is
  1,3-benzodioxol-5-yl, m.p. 53°–54°
  4-methoxyphenyl
  2,4-dimethoxyphenyl
  2-benzyloxy-4-methoxyphenyl
  2-hydroxy-4-methoxy-carboxy-carboxymethoxy-4-methoxyphenyl
  2-hydroxyethyloxy-4-methoxyphenyl
4-T-1,2-dihydro-6-ethoxy-1-(4-methoxybenzyl)-2-oxoquinoline-3-carboxylic acids in which T is
  1,3-benzodioxol-5-yl, m.p. 209°–210°
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-6-ethoxy-2-(4-methoxybenzyloxy)quinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-1,2-dihydro-6-ethoxy-1-(3,4-methylenedioxybenzyl)-2-oxoquinoline-3-carboxylic acids in which T is
  1,3-benzodioxol-5-yl, m.p. 210°–111°
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-6-ethoxy-2-(3,4-methylenedioxybenzyloxy)quinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-1,2-dihydro-6-ethoxy-1-(6-chloro-3,4-methylenedioxybenzyl)-2-oxoquinoline-3-carboxylic acids in which T is
  1,3-benzodioxol-5-yl, m.p. 247°–248°
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-6-ethoxy-2-(6-chloro-3,4-methylenedioxybenzyloxy)quinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-1,2-dihydro-6-ethoxy-1-benzyl-2-oxoquinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-6-ethoxy-2-benzyloxyquinoline-3-carboxylic acids in which T is
  3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-1,2-dihydro-6-ethoxy-1-(2-methylthiobenzyl)-2-oxoquinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-6-ethoxy-2-(2-methylthiobenzyloxy)quinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-1,2-dihydro-6-ethoxy-1-(2-methylsulfinylbenzyl)-2-oxoquinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl 2-hydroxyethyloxy-4-methoxyphenyl
4-T-6-ethoxy-2-(2-methylsulfinylbenzyloxy)quinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-1,2-dihydro-6-ethoxy-1-(2-methylsulfonylbenzyl)-2-oxoquinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-6-ethoxy-2-(2-methylsulfonylbenzyloxy)quinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-1,2-dihydro-6-ethoxy-1-(2,3-dimethoxybenzyl)-2-oxoquinoline-3-carboxylic acids in which T is
  1,3-benzodioxol-5-yl, m.p. 211°–212°
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-6-ethoxy-2-(2,3-dimethoxybenzyloxy)quinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-1,2-dihydro-6-ethoxy-1-(2,3-methylenedioxybenzyl)-2-oxoquinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-6-ethoxy-2-(2,3-methylenedioxybenzyloxy)quinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-1,2-dihydro-6-ethoxy-1-(2,1,3-benzothiadiazole-5-methyl)-2-oxoquinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-6-ethoxy-2-(2,1,3-benzothiadiazole-5-methyloxy)-quinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-1,2-dihydro-1-(2-methoxybenzyl)-2-oxoquinoline-3-carboxylic acids in which T is
  1,3-benzodioxol-5-yl, m.p. 231°–232°
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-2-(2-methoxybenzyloxy)quinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-1,2-dihydro-1-(3-methoxybenzyl)-2-oxoquinoline-3-carboxylic acids in which T is
  1,3-benzodioxol-5-yl, m.p. 162°–163°
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl
  2-hydroxyethyloxy-4-methoxyphenyl
4-T-2-(3-methoxybenzyloxy)quinoline-3-carboxylic acids in which T is
  1,3-benzodioxol-5-yl
  4-methoxyphenyl
  2,4-dimethoxyphenyl
  2-benzyloxy-4-methoxyphenyl
  2-hydroxy-4-methoxyphenyl
  2-carboxymethoxy-4-methoxyphenyl 2-hydroxyethyloxy-4-methoxyphenyl
4-T-1,2-dihydro-1-(4-methoxybenzyl)-2-oxoquinoline-3-carboxylic acids in which T is
    1,3-benzodioxol-5-yl, m.p. 222°–223°
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-2-(4-methoxybenzyloxy)quinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-1-(3,4-methylenedioxybenzyl)-2-oxoquinoline-3-carboxylic acids in which T is
    1,3-benzodioxol-5-yl, m.p. 216°–217°
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-2-(3,4-methylenedioxybenzyloxy)quinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-1-(6-chloro-3,4-methylenedioxybenzyl)-2-oxoquinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-2-(6-chloro-3,4-methylenedioxybenzyloxy)quinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-1-benzyl-2-oxoquinoline-3-carboxylic acids in which T is
    1,3-benzodioxol-5-yl, m.p. 184°–185°
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-2-benzyloxyquinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-1-(2-methylthiobenzyl)-2-oxoquinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-2-(2-methylthiobenzyloxy)quinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-1-(2-methylsulfinylbenzyl)-2-oxoquinoline-3-carboxylic acids in which T is
    3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-2-(2-methylsulfinylbenzyloxy)quinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-1-(2-methylsulfonylbenzyl)-2-oxoquinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl 4-T-2-(2-methylsulfonylbenzyloxy)quinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-1-(2,3-dimethoxybenzyl)-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-2-(2,3-dimethoxybenzyloxy)quinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-1-(2,3-methylenedioxybenzyl)-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-2-(2,3-methylenedioxybenzyloxy)quinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-1-(2,1,3-benzothiadiazole-5-methyl)-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-2-(2,1,3-benzothiadiazole-5-methyloxy)quinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-1-(2-methoxybenzyl)-6-propionyl-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-2-(2-methoxybenzyloxy)-6-propionylquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-1-(3-methoxybenzyl)-6-propionyl-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-2-(3-methoxybenzyloxy)-6-propionylquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-1-(4-methoxybenzyl)-6-propionyl-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-2-(4-methoxybenzyloxy)-6-propionylquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-1-(3,4-methylenedioxybenzyl)-6-propionyl-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-2-(3,4-methylenedioxybenzyloxy)-6-propionylquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-1-(6-chloro-3,4-methylenedioxybenzyl)-6-propionyl-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-2-(6-chloro-3,4-methylenedioxybenzyloxy)-6-propionylquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-1-benzyl-6-propionyl-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-2-benzyloxy-6-propionylquinoline-3-carboxylic acids, in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-6,7-dimethoxy-1-(2-methoxybenzyl)-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-6,7-dimethoxy-2-(2-methoxybenzyloxy)quinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-6,7-dimethoxy-1-(3-methoxybenzyl)-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-6,7-dimethoxy-2-(3-methoxybenzyloxy)quinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-6,7-dimethoxy-1-(4-methoxybenzyl)-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-6,7-dimethoxy-2-(4-methoxybenzyloxy)quinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-6,7-dimethoxy-1-(3,4-methylenedioxybenzyl)-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-6,7-dimethoxy-2-(3,4-methylenedioxybenzyloxy) quinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-6,7-dimethoxy-1-(6-chloro-3,4-methylenedioxybenzyl)-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-6,7-dimethoxy-2-(6-chloro-3,4-methylenedioxybenzyloxy)quinoline-3-carboxylic acids in which T-is
- 1,3-benzodioxol-5-yl
- 4-methoxyphenyl
- 2,4-dimethoxyphenyl
- 2
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-6,7-dimethoxy-1-benzyl-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-2-benzyloxy-6,7-dimethoxyquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-6,7-dimethyl-1-(2-methoxybenzyl)-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-6,7-dimethyl-2-(2-methoxybenzyloxy)quinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-6,7-dimethyl-1-(3-methoxybenzyl)-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-6,7-dimethyl-2-(3-methoxybenzyloxy)quinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-6,7-dimethyl-1-(4-methoxybenzyl)-2-oxoquinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-6,7-dimethyl-2-(4-methoxybenzyloxy)quinoline-3-carboxylic acids in which T is
- 1,3-benzodioxol-5-yl
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-1,2-dihydro-6,7-dimethyl-1-(3,4-methylenedioxybenzyl)-2-oxoquinoline-3-carboxylic acids in which T is
- 1,3-benzodioxol-5-yl,
- 4-methoxyphenyl
- 2,4-dimethoxyphenyl
- 2-benzyloxy-4-methoxyphenyl
- 2-hydroxy-4-methoxyphenyl
- 2-carboxymethoxy-4-methoxyphenyl
- 2-hydroxyethyloxy-4-methoxyphenyl 4-T-6,7-dimethyl-2-(3,4-methylenedioxybenzyloxy)-quinoline-3-carboxylic acids in which T is
- 1,3-benzodioxol-5-yl
- 4-methoxyphenyl
- 2,4-dimethoxyphenyl
- 2-benzyloxy-4-methoxyphenyl 2-hydroxy-4-methoxyphenyl
2-carboxymethoxy-4-methoxyphenyl
2-hydroxyethyloxy-4-methoxyphenyl
4-T-1,2-dihydro-6,7-dimethyl-1-(6-chloro-3,4-methylenedioxybenzyl)-2-oxoquinoline-3-carboxylic acids in which T is
   1,3-benzodioxol-5-yl
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-6,7-dimethyl-2-(6-chloro-3,4-methylenedioxybenzyloxy)quinoline-3-carboxylic acids in which T is
   1,3-benzodioxol-5-yl
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-1,2-dihydro-6,7-dimethyl-1-benzyl-2-oxoquinoline-3-carboxylic acids in which T is
   3-benzodioxol-5-yl
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-2-benzyloxy-6,7-dimethylquinoline-3-carboxylic acids in which T is
   1,3-benzodioxol-5-yl
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-1,2-dihydro-6-ethyl-1-(2-methoxybenzyl)-2-oxoquinoline-3-carboxylic acids in which T is
   1,3-benzodioxol-5-yl, m.p. 225°–226°
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-6-ethyl-2-(2-methoxybenzyloxy)quinoline-3-carboxylic acids in which T is
   1,3-benzodioxol-5-yl
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-1,2-dihydro-6-ethyl-(3-methoxybenzyl)-2-oxoquinoline-3-carboxylic acids in which T is
   1,3-benzodioxol-5-yl
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-6-ethyl-2-(3-methoxybenzyloxy)quinoline-3-carboxylic acids in which T is
   1,3-benzodioxol-5-yl
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-1,2-dihydro-6-ethyl-1-(4-methoxybenzyl)-2-oxoquinoline-3-carboxylic acids in which T is
   1,3-benzodioxol-5-yl
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-6-ethyl-2-(4-methoxybenzyloxy)quinoline-3-carboxylic acids in which T is
   1,3-benzodioxol-5-yl
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-1,2-dihydro-6-ethyl-1-(3,4-methylenedioxybenzyl)-2-oxoquinoline-3-carboxylic acids in which T is
   1,3-benzodioxol-5-yl
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-6-ethyl-2-(3,4-methylenedioxybenzyloxy)quinoline-3-carboxylic acids in which T is
   1,3-benzodioxol-5-yl
   4-methoxyphenyl
   2,4-dimethoxyphenyl
   2-benzyloxy-4-methoxyphenyl
   2-hydroxy-4-methoxyphenyl
   2-carboxymethoxy-4-methoxyphenyl
   2-hydroxyethyloxy-4-methoxyphenyl
4-T-1,2-dihydro-6-ethyl-1-(6-chloro-3,4-methylenedioxybenzyl)-2-oxoquinoline-3-carboxylic acids in which T is
   1,3-benzodioxol-5-yl
   4-methoxyphenyl 2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
4-T-6-ethyl-2-(6-chloro-3,4-methylenedioxybenzyloxy)quinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-6-ethyl-1-benzyl-2-oxoquinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-6-ethyl-2-benzyloxyquinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-6-ethyl-1-(2methylthiobenzyl)-2oxoquinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-6-ethyl-2-(2-methylthiobenzyloxy)quinoline-3-carboxylic acids in which T is
    1,3-benzodioxol-5-y
    4-methoxyphenyl
    4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-6-ethyl-1-(2-methylsulfinylbenzyl)-2-oxoquinoline-3-carboxylic acids in which T is
    3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-6-ethyl-2-(2-methylsulfinylbenzyloxy)quinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-6-ethyl-1-(2-methylsulfonylbenzyl)-2-oxoquinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-6-ethyl-2-(2-methylsulfonylbenzyloxy)quinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-6-ethyl-1-(2,3-dimethoxybenzyl)-2-oxoquinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-6-ethyl-2-(2,3-dimethoxybenzyloxy)quinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-1,2-dihydro-6-ethyl-1-(2,3-methylenedioxybenzyl)-2-oxoquinoline-3-carboxylic acids in which T is
    1,3-benzodioxol-5-yl
    4-methoxyphenyl
    2,4-dimethoxyphenyl
    2-benzyloxy-4-methoxyphenyl
    2-hydroxy-4-methoxyphenyl
    2-carboxymethoxy-4-methoxyphenyl
    2-hydroxyethyloxy-4-methoxyphenyl
4-T-6-ethyl-2-(2,3-methylenedioxybenzyloxy)quinoline-3-carboxylic acids in which T is
    1,3-benzodioxol-5-yl
    4-methoxyphenyl 2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
4-T-1,2-dihydro-6-ethyl-1-(2,1,3-benzothiadiazole-5-methyl)-2-oxoquinoline-3-carboxylic acids in which T is
1,3-benzodioxol-5-yl)
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
4-T-6-ethyl-2-(2,1,3-benzothiadiazole-5-methyloxy)quinoline-3-carboxylic acids in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

EXAMPLE 3

10 ml of a 2M aqueous sodium carbonate solution and 1.52 g of 4-methoxyphenylboronic acid in 25 ml of methanol are added to a solution of 4.1 g of methyl 4-(1,3-benzodioxol-5-yl)-2-chloroquinoline-3-carboxylate and 0.25 g of tetrakis(triphenylphosphine)palladium(0) in 50 ml of toluene, and the mixture is boiled under reflux under an inert gas atmosphere for 1 hour. The usual working up results in methyl 4-(1,3-benzodioxol-5-yl)-2-(4-methoxyphenyl)quinoline-3-carboxylate.

EXAMPLE 4

A solution of 3.8 g of methyl 4-(1,3-benzodioxol-5-yl)-2-chloroquinoline-3-carboxylate and 3.1 g of caesium carbonate in 40 ml of DMF is stirred with a solution of 1.7 g of 3,4-methylenedioxyphenol in 20 ml of dichloromethane overnight. The usual working up results in methyl 4-(1,3-benzodioxol-5=yl)-2-(3,4-methylenedioxyphenoxy)quinoline-3-carboxylate.

EXAMPLE 5

A solution of 1 g of 1,2-dihydro-1-(2,3-dimethoxybenzyl)-4-(4-methoxyphenyl)-2-oxo-6-nitroquinoline-3-carboxylic acid in 25 ml of methanol is hydrogenated to standstill on 1 g of Raney nickel under atmospheric pressure and at 20°. Filtration and removal of the solvent result in 6-amino-1,2-dihydro-1-(2,3-dimethoxybenzyl)-4-(4-methoxyphenyl)-2-oxoquinoline-3-carboxylic acid.

EXAMPLE 6

1 ml of freshly distilled acetaldehyde is added to a solution of 6 g of 6-amino-1,2-dihydro-1-( 2,3-dimethoxybenzyl)-4-(4-methoxyphenyl)-2-oxoquinoline-3-carboxylic acid and 0.5 g of titanium tetrachloride in 100 ml of methanol. Then 4 g of sodium cyanoborohydride are added and the mixture is stirred for 30 hours. Addition of 50% concentrated hydrochloric acid and the usual working up result in 6-ethylamino-1,2-dihydro-1-(2,3-dimethoxybenzyl)-4-(4-methoxyphenyl)-2-oxoquinoline-3-carboxylic acid.

EXAMPLE 7

5 ml of thionyl chloride and 1.57 g of phenylsulfonamide are added to a solution of 4.85 g of 4-(1,3-benzodioxol-5-yl)-1,2-dihydro-1-(3,4-methylenedioxybenzyl)-2-oxoquinoline-3-carboxylic acid and 0.2 g of dimethylaminopyridine in 50 ml of pyridine. The mixture is stirred for 10 hours, and the usual working up results in 4-(1,3-benzodioxol-5-yl)-1,2-dihydro-1-(3,4-methylenedioxybenzyl)-2-oxo-3-(phenylsulfonamidocarbonyl)quinoline.

EXAMPLE 8

In analogy to Example 1, reaction of methyl 4-(1,3-benzodioxol-5-yl)1,2-dihydro-2-oxoquinoline-3-acetate (obtainable by reaction of 1-amino-2-(3,4-methylenedioxybenzoyl)-4-ethoxybenzene and methyl succinyl chloride) and "A" results in the N-alkylation product methyl 4-(1,3-benzodioxol-5-yl)1,2-dihydro-1-(2-methoxybenzyl)-2-oxoquinoline-3-acetate, m.p. 71°–72° and the O-alkylation product methyl 4-(1,3-benzodioxol-5-yl)-2-(2-methoxybenzyloxy)quinoline-3-acetate.

Analogously, from the following methyl 4-T-1,2-dihydro-2-oxoquinoline-3-acetates in which T is
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
with "A" are obtained the following methyl 4-T-1,2-dihydro-1-(2-methoxybenzyl)-2-oxoquinoline-3-acetates in which T is
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
and the following methyl 4-T-2-(2-methoxybenzyloxy)quinoline-3-acetates in which T is
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl.

Analogously, reaction of 3,4-methylenedioxybenzyl chloride with the following methyl 4-T-1,2-dihydro-2-oxoquinoline-3-acetates in which T is
1,3-benzodioxol-5-yl
4-methoxyphenyl
2,4-dimethoxyphenyl
2-benzyloxy-4-methoxyphenyl
2-hydroxy-4-methoxyphenyl
2-carboxymethoxy-4-methoxyphenyl
2-hydroxyethyloxy-4-methoxyphenyl
results in the following methyl 4-T-1,2-dihydro-1-(3,4-methylenedioxybenzyl)-2-oxoquinoline-3-acetates in which T is 1,3-benzodioxol-5-yl, m.p. 79°–80°

4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl and the following methyl 4-T-2-(3,4-methylenedioxybenzyloxy)quinoline-3-acetates in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl.

Subsequent hydrolysis, in analogy to Example 2, of the esters listed above results in the following 4-T-1,2-dihydro-1-(2-methoxybenzyl)-2-oxoquinoline-3-acetic acids in which T is 1,3-benzodioxol-5-yl, m.p. 165°–166°

4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl 4-T-2-(2-methoxybenzyloxy)quinoline-3-acetic acids in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl 4-T-1,2-dihydro-1-(3,4-methylenedioxybenzyl)-2-oxoquinoline-3-acetic acids in which T is 1,3-benzodioxol-5-yl, m.p. 186°–187°

4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl and 4-T-2-(3,4-methylenedioxybenzyloxy)quinoline-3-acetic acids in which T is 1,3-benzodioxol-5-yl 4-methoxyphenyl 2,4-dimethoxyphenyl 2-benzyloxy-4-methoxyphenyl 2-hydroxy-4-methoxyphenyl 2-carboxymethoxy-4-methoxyphenyl 2-hydroxyethyloxy-4-methoxyphenyl.

EXAMPLE 9

In analogy to Example 2, hydrolysis of the following esters methyl 4-(1,3-benzodioxol-5-yl)1,2-dihydro-5,6-dimethoxy-1-(2-methoxybenzyl)-2-oxoquinoline-3-carboxylate, m.p. 210°–211°, methyl 4-(1,3-benzodioxol-5-yl)-1,2-dihydro-5,6-dimethoxy-1-(2-methylbenzyl)-2-oxoquinoline-3-carboxylate, methyl 4-(1,3-benzodioxol-5-yl)1,2-dihydro-5,6-dimethoxy-1-(2,5-dimethoxybenzyl)-2-oxoquinoline-3-carboxylate, methyl 4-(1,3-benzodioxol-5-yl)-1,2-dihydro-5,6-dimethoxy-1-(3,4,5-trimethoxybenzyl)-2-oxoquinoline-3-carboxylate, methyl 4-(4-methoxyphenyl)1,2-dihydro-6-ethoxy-1-(2,5-dimethoxybenzyl)-2-oxoquinoline-3-carboxylate, methyl 4-(1,3-benzodioxol-5-yl)-1,2-dihydro-6-ethyl-1-(2,5-dimethoxybenzyl)-2-oxoquinoline-3-carboxylate, results in the following compounds 4-(1,3-benzodioxol-5-yl)1,2-dihydro-5,6-dimethoxy-1-(2-methoxybenzyl)-2-oxoquinoline-3-carboxylic acid, m.p. 250°, 4-(1,3-benzodioxol-5-yl)-1,2-dihydro-5,6-dimethoxy-1-(2-methylbenzyl)-2-oxoquinoline-3-carboxylic acid, m.p. 247°–249°, 4-(1,3-benzodioxol-5-yl)-1,2-dihydro-5,6-dimethoxy-1-(2,5-dimethoxybenzyl)-2-oxoquinoline-3-carboxylic acid, m.p.233°, 4-(1,3-benzodioxol-5-yl)-1,2-dihydro-5,6-dimethoxy-1-(3,4,5-trimethoxybenzyl)-2-oxoquinoline-3-carboxylic acid, m.p 269.3°, 4-(4-methoxyphenyl)-1,2-dihydro-6-ethoxy-1-(2,5-dimethoxybenzyl)-2-oxoquinoline-3-carboxylic acid, m.p. 178°–179°, 4-(1,3-benzodioxol-5-yl)1,2-dihydro-6-ethyl-1-(2,5-dimethoxybenzyl)-2-oxoquinoline-3-carboxylic acid, m.p. 199.2°.

The following examples relate to pharmaceutical compositions:

Example A

Vials

A solution of 100 g of an active substance of the formula I and 5 g of disodium hydrogen phosphate in 3 l of double-distilled water is adjusted to a pH of 6.5 with 2 n hydrochloric acid, sterilized by filtration, dispensed into vials and lyophilized and sealed under sterile conditions. Each vial comprises 5 mg of active substance.

Example B

Suppositories

A mixture of 20 g of an active substance of the formula I with 100 g of soya lecithin and 1400 g of cocoa butter is melted, poured into moulds and left to cool. Each suppository comprises 20 mg of active substance.

Example C

Solution

A solution is prepared from 1 g of an active substance of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water. The pH is adjusted to 6.8, and the solution is made up to 1 l and radiation-sterilized. This solution can be used in the form of eyedrops.

Example D

Ointment 500 mg of an active substance of the formula I are mixed with 99.5 g of petrolatum under aseptic conditions.

Example E

Tablets

A mixture of 1 kg of active substance of the formula I, 4 kg of lactose, 1.2 kg of potato starch, 0.2 kg of talc and 0.1 kg of magnesium stearate is compressed to tablets in a conventional way so that each tablet comprises 10 mg of active substance.

Example F

Coated tablets

Tablets are compressed in analogy to Example E and are then coated in a conventional way with a coating of sucrose, potato starch, talc, tragacanth and colourant.

Example G

Capsules 2 kg of active substance of the formula I are packed into hard gelatin capsules in a conventional way so that each capsule comprises 20 mg of the active substance.

Example H

Ampoules

A solution of 1 kg of active substance of the formula I in 60 l of double-distilled water is sterilized by filtration, dispensed into ampoules and lyophilized and sealed under sterile conditions. Each ampoule comprises 10 mg of active substance.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of the formula

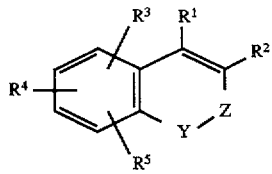

in which

—Y—Z— is —NR$^7$—CO—, —N=C(OR$^7$)— or —N=CR$^8$—,

R$^1$ is Ar,

R$^2$ is COOR$^6$, (CH$_2$)$_n$COOR$^6$, CN, 1H-tetrazol-5-yl or CONHSO$_2$Ar,

R$^3$, R$^4$, R$^5$ are each, independently of one another, R$^6$, OR$^6$, S(O)$_m$R$^6$, Hal, NO$_2$, NR$^6$R$^6$, NHCOR$^6$, NHSO$_2$R$^6$, OCOR$^6$, COR$^6$, COOR$^6$, or CN or R$^3$ R$^4$ are together optionally also an O(CH$_2$)$_n$O group, R$^6$, R$^{6\prime}$ are each, independently of one another, H, alkyl with 1 to 6 C atoms, benzyl or phenyl, R$^7$ is (CH$_2$)$_n$Ar, R$^8$ is OAr, Ar are each independently phenyl which is unsubstituted or substituted once, twice or three times by R$^9$, R$^{10}$ or R$^{11}$, or unsubstituted naphthyl or

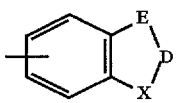

group
which is unsubstituted or substituted once or twice in the phenyl moiety by R$^9$ or R$^{10}$ or a

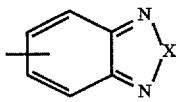

group
which is unsubstituted or substituted once or twice in the cyclohexadienyl moiety by R$^9$ or R$^{10}$, R$^9$, R$^{10}$, R$^{11}$ are each, independently of one another, R$^6$, OR$^6$, Hal, CF$_3$, OCF$_3$, OCHF$_2$, OCH$_2$F, NO$_2$, NR$^6$R$^6$, NHCOR$^6$, CN, NHSO$_2$R$^6$, COOR$^6$, COR$^6$, CONHSO$_2$Ar, O(CH$_2$)$_n$R$^2$, O(CH$_2$)$_n$OR$^6$ or S(O)$_m$R$^6$, E is CH$_2$, S or O, D is carbonyl or, $_n$, X is O or S, Hal is F, Cl, Br or I, m is 0, 1 or 2, n is 1, 2 or 3, and their salts.

2. A compound of claim 1, which compound is:
   a) 4-(1,3-benzodioxol-5-yl)-1,2-dihydro-1-(2-methoxybenzyl)-2-oxoquinoline-3-carboxylic acid;
   b) 4-(1,3-benzodioxol-5-yl)-1,2-dihydro-1-(4-methoxybenzyl)-2-oxoquinoline-1-carboxylic acid;
   c) 4-(1,3-benzodioxol-5-yl)-1,2-dihydro-1-(3,4-methylenedioxybenzyl)-2-oxoquinoline-3-carboxylic acid;
   d) 4-(1,3-benzodioxol-5-yl)-1,2-dihydro-1-(2-methoxybenzyl)-2-oxoquinoline-3-acetic acid;
   e) 4-(1,3-benzodioxol-5-yl)-1,2-dihydro-1-(3,4-methylenedioxybenzyl)-2-oxoquinoline-3-acetic acid;
   f) 4-(1,3-benzodioxol-5-yl)-1,2-dihydro-6-ethoxy-1-(2-methoxybenzyl)-2-oxoquinoline-3-carboxylic acid;
   g) 4-(1,3-benzodioxol-5-yl)-1,2-dihydro-6-ethoxy-1-(4-methoxybenzyl)-2-oxoquinoline-3-carboxylic acid;
   h) 4-(1,3-benzodioxol-5-yl)-1,2-dihydro-6-ethoxy-1-(6-chloro-3,4-methylenedioxybenzyl)-2-oxoquinoline-3-carboxylic acid;
   i) 4-(1,3-benzodioxol-5-yl)-1,2-dihydro-6-ethoxy-1-(3,4-methylenedioxybenzyl)-2-oxoquinoline-3-carboxylic acid;
   j) 4-(1,3-benzodioxol-5-yl)-1,2-dihydro-6-ethoxy-1-(3-methoxybenzyl)-2-oxoquinoline-3-carboxylic acid.

3. A process for the production of a pharmaceutical composition, which comprises combining a compound of the formula I according to claim 1 and/or one of its physiologically acceptable salts with at least one solid, liquid or semiliquid vehicle or ancillary substance to provide the compound in a suitable pharmaceutical dosage form.

4. A pharmaceutical composition comprising a pharmaceutically effective amount of at least one compound of the formula I according to claim 1 and/or one of its physiologically acceptable salts.

5. A method for inducing an endothelin receptor antagonist effect in a patient which comprises administering to the patient an endothelin receptor antagonist effective amount of at least one compound of the formula I of claim 1 and/or one of its physiologically acceptable salts.

6. The method of claim 5, wherein the compound of tile formula I of claim 1 and/or one of its physiologically acceptable salts is administered in a daily dose of from about 0.02 to 10 mg/kg.

7. A method for controlling a disease controllable by endothelin receptor antagonist activity which comprises administering an endothelin receptor antagonist effective amount of at least one compound of the formula I of claim 1 and/or one of its physiologically acceptable salts.

8. The method of claim 7, wherein the compound of the formula I of claim 1 and/or one of its physiologically acceptable salts is administered in a daily dose of from about 0.02 to 10 mg/kg.

9. The method of claim 7, wherein the disease is hypertension; heart failure; coronary heart disease; renal, cerebral or myocardial ischaemia; renal insufficiency; cerebral infarct; subarachnoid hemorrhage; arteriosclerosis; pulmonary hypertension; inflammation; asthma; prostate hyperplasia; endotoxic shock; or complications following administration of cyclosporin.

10. The method of claim 7, wherein the disease is a cardiac, circulatory or vascular disorder.

11. The method of claim 7, wherein the disease is hypertension or heart failure.

12. The method of claim 7, wherein the disease is hypertension and/or cardiac insufficiency.

* * * * *